(12) United States Patent
Yan

(10) Patent No.: US 12,734,018 B2
(45) Date of Patent: Sep. 15, 2026

(54) METHOD FOR GENERATING RESTARTED ORTHODONTIC TREATMENT PLAN

(71) Applicant: HANGZHOU CHOHOTECH CO., LTD., Hangzhou City (CN)

(72) Inventor: Qianhang Yan, Hangzhou City (CN)

(73) Assignee: HANGZHOU CHOHOTECH CO., LTD., Hangzhou City (CN)

( * ) Notice: Subject to any disclaimer, the term of this patent is extended or adjusted under 35 U.S.C. 154(b) by 483 days.

(21) Appl. No.: 18/013,531

(22) PCT Filed: Mar. 30, 2021

(86) PCT No.: PCT/CN2021/083969
§ 371 (c)(1),
(2) Date: Dec. 28, 2022

(87) PCT Pub. No.: WO2022/001247
PCT Pub. Date: Jan. 6, 2022

(65) Prior Publication Data

US 2023/0255726 A1 Aug. 17, 2023

(30) Foreign Application Priority Data

Jun. 28, 2020 (CN) ......................... 202010596548.2

(51) Int. Cl.
*A61C 7/00* (2006.01)
*G16H 20/30* (2018.01)
*G16H 50/50* (2018.01)

(52) U.S. Cl.
CPC ............. *A61C 7/002* (2013.01); *G16H 20/30* (2018.01); *G16H 50/50* (2018.01); *A61C 2007/004* (2013.01)

(58) Field of Classification Search
CPC .. A61C 7/002; A61C 2007/004; G16H 20/30; G16H 50/50; G16H 20/40; G06T 7/33;
(Continued)

(56) References Cited

U.S. PATENT DOCUMENTS

2001/0002310 A1* 5/2001 Chishti .................... A61C 7/08 345/20
2002/0042038 A1* 4/2002 Miller .................... G16H 50/50 433/215

(Continued)

FOREIGN PATENT DOCUMENTS

CN 105726142 A 7/2016
CN 106618760 A 5/2017
CN 111265317 A 6/2020

*Primary Examiner* — Heidi M Eide
*Assistant Examiner* — Lina Faraj
(74) *Attorney, Agent, or Firm* — Birch, Stewart, Kolasch & Birch, LLP

(57) ABSTRACT

One aspect of the present application provides a method for generating restarted orthodontic treatment plan, the method comprises: obtaining a first group of M 3D digital models of teeth which represent the last M successive tooth arrangements in a previous orthodontic treatment plan of a dentition, respectively; obtaining a first 3D digital model of teeth which represents the tooth arrangement of the dentition upon restart of orthodontic treatment; and generating a restarted orthodontic treatment plan based on the first 3D digital model of teeth and the first group of 3D digital models of teeth, wherein an orthodontic treatment plan comprises a plurality of successive tooth arrangements from an initial tooth arrangement to a target tooth arrangement, and represent the path of an orthodontic treatment.

4 Claims, 3 Drawing Sheets

(58) Field of Classification Search
CPC ..... G06T 17/00; G06T 7/344; G06T 2207/36; G06T 2210/41
See application file for complete search history.

(56) References Cited

U.S. PATENT DOCUMENTS

| | | | | |
|---|---|---|---|---|
| 2005/0048432 | A1* | 3/2005 | Choi | A61C 7/002 433/24 |
| 2008/0305453 | A1* | 12/2008 | Kitching | A61C 7/08 433/213 |
| 2010/0151404 | A1* | 6/2010 | Wu | G06T 7/60 433/24 |
| 2013/0273491 | A1* | 10/2013 | Isaacson | A61C 7/002 433/24 |
| 2019/0314116 | A1 | 10/2019 | Kitching et al. | |
| 2020/0000555 | A1 | 1/2020 | Yuryev et al. | |
| 2020/0037848 | A1 | 2/2020 | Ozerov et al. | |

* cited by examiner

100 a step closest to the tooth arrangement upon restart of orthodontic treatment is identified in the initial teeth aligning plan

101 a restarted orthodontic plan is generated based on the identified step to the last step of the initial teeth aligning plan and a 3D digital model of teeth representing the tooth arrangement upon restart of orthodontic treatment

101 the 3D digital model of teeth representing the tooth arrangement upon restart of orthodontic treatment and the 3D digital models of teeth in the initial teeth aligning plan are aligned based on selected anchor teeth

1011 tooth models of the 3D digital models of teeth of the initial teeth aligning plan are replaced with corresponding tooth models of the 3D digital model of teeth representing the tooth arrangement upon restart of orthodontic treatment

1013 a 3D digital model of teeth which is closest to the 3D digital model of teeth representing the tooth arrangement upon restart of orthodontic treatment is identified in the initial teeth aligning plan

103 the 3D digital model of teeth of the initial teeth aligning plan with replaced tooth models is optimized in terms of collision and gap to obtain a 3D digital model of teeth representing the target tooth arrangement of the restarted teeth aligning plan — 1031

↓ the restarted teeth aligning plan is generated based on two 3D digital models of teeth representing its initial tooth arrangement and target tooth arrangement respectively and a selected section of the initial teeth aligning plan — 1033

FIG. 1B

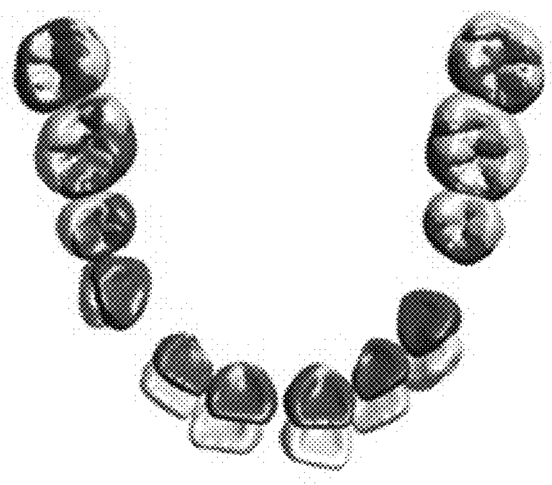

FIG. 2

METHOD FOR GENERATING RESTARTED ORTHODONTIC TREATMENT PLAN

CROSS REFERENCE TO RELATED APPLICATIONS

The present application is a 35 U.S.C. § 371 National Phase conversion of International (PCT) Patent Application No. PCT/CN2021/083969, filed on Mar. 30, 2021, which claims the priority of Chinese Application No. 202010596548.2 filed on Jun. 28, 2020, the disclosure of which is incorporated by reference herein. The PCT International Patent Application was filed and published in Chinese.

FIELD OF THE APPLICATION

The present application generally relates to a method for generating restarted orthodontic treatment plan.

BACKGROUND

Due to advantages on aesthetic appearance, convenience and hygiene etc., shell-shaped tooth repositioners made of polymer materials become more and more popular. Usually, an orthodontic treatment using shell shaped tooth repositioners requires a series of successive shell-shaped tooth repositioners. Usually the geometries of teeth-receiving cavities of these shell-shaped tooth repositioners substantially match tooth arrangements to be achieved by corresponding repositioning steps.

During an orthodontic treatment using shell-shaped tooth repositioners, a patient's tooth arrangement might significantly deviate from an initial treatment plan, in such case the patient shall not use the designs of shell-shaped tooth repositioners of the subsequent steps of the treatment plan, and it is necessary to redesign a subsequent treatment plan according to the patient's current conditions, i.e., restart an orthodontic treatment.

A conventional method for restarting an orthodontic treatment is that a professional adjusts the original target tooth arrangement according to a 3D digital model of the patient's current teeth to obtain a new target tooth arrangement, and designs a plurality of successive intermediate tooth arrangements from the patient's current tooth arrangement to the target tooth arrangement. Since the conventional method mainly relies on manual operations, the whole process from determining a restarting step to designing and adjusting the new treatment plan consumes immense manpower, and the quality of the new treatment plan is mainly dependent on the professional's experience and expertise.

Therefore, it is necessary to provide a new method for generating restarted orthodontic plan.

SUMMARY

One aspect of the present application provides a method for generating restarted orthodontic treatment plan, the method comprises: obtaining a first group of M 3D digital models of teeth which represent the last M successive tooth arrangements in a previous orthodontic treatment plan of a dentition, respectively; obtaining a first 3D digital model of teeth which represents the tooth arrangement of the dentition when the orthodontic treatment is restarted; and generating a restarted orthodontic treatment plan based on the first 3D digital model of teeth and the first group of 3D digital models of teeth, wherein M is a natural number greater than 2, and an orthodontic treatment plan comprises a plurality of successive tooth arrangements from an initial tooth arrangement to a target tooth arrangement, and represents the path of an orthodontic treatment.

It is given that the previous orthodontic treatment plan comprises N successive 3D digital models of teeth respectively representing N successive tooth arrangements from an initial tooth arrangement to a target tooth arrangement. In one embodiment, the first group of 3D digital model of teeth may comprise all successive 3D digital models of teeth in the previous orthodontic treatment plan i.e. N=M. In another embodiment, the first group of 3D digital models of teeth may only comprise the last plurality of successive 3D digital models of teeth in the previous orthodontic treatment plan, namely, N>M.

In some embodiments, the method for generating restarted orthodontic treatment plan may further comprise: replacing at least one tooth model in the first group of 3D digital models of teeth with corresponding tooth model in the first 3D tooth digital model, to obtain a second group of M 3D digital models of teeth, the restarted orthodontic treatment plan is generated based on the first 3D digital model of teeth and the second group of 3D digital models of teeth.

In some embodiments, the replacement of the at least one tooth model may be based on an ICP algorithm.

In some embodiments, the method for generating restarted orthodontic treatment plan may further comprise: performing collision and gap optimization on the last one in the second group of 3D digital models of teeth to obtain a second 3D digital model of teeth representing a target tooth arrangement of the restarted orthodontic treatment plan, the restarted orthodontic treatment plan is generated based on the first 3D digital model of teeth, the second group of 3D digital models of teeth and the second 3D digital model of teeth.

In some embodiments, the method for generating restarted orthodontic treatment plan may further comprise: for each tooth to be repositioned, identifying in the second group of 3D digital models of teeth a 3D digital model of teeth in which the pose of the tooth to be repositioned is closest to that in the first 3D digital model; calculating the poses of each tooth to be repositioned in steps of the restarted orthodontic treatment plan, based on a pose difference of the tooth to be repositioned between the first 3D tooth digital model and the corresponding identified 3D digital model of teeth, the first one along the second group of 3D digital models of teeth that is identified to the last one along the second group of 3D digital models of teeth, and a pose difference of the tooth to be repositioned between the second 3D tooth digital model and the last one along the second group of 3D digital models of teeth; and generating the restarted orthodontic treatment plan based on the poses of the teeth to be repositioned in the steps of the restarted orthodontic treatment plan.

In some embodiments, for each tooth to be repositioned, the pose of the tooth to be repositioned in a corresponding 3D digital model of teeth identified from the second group of 3D digital models of teeth is closer to a target pose than its pose in the first 3D tooth digital model.

In some embodiments, the method for generating restarted orthodontic treatment plan may further comprise: calculating the poses of each tooth to be repositioned in key frames of the restarted orthodontic treatment plan, based on a pose difference of the tooth to be repositioned between the first 3D digital model of teeth and the corresponding identified 3D digital model of teeth, the first one along the second group of 3D digital models of teeth that is identified to the last one along the second group of 3D digital models of teeth, and pose differences of the tooth to be repositioned between the second 3D digital model of teeth and the last one along the second group of 3D digital models of teeth; and interpolating based on the poses of the teeth to be repositioned in the key frames in the restarted orthodontic treatment plan, to obtain poses of the teeth to be repositioned in each step of the restarted orthodontic treatment plan, wherein a key frame is a step in which any tooth start or stops a movement.

In some embodiments, the restarted orthodontic treatment plan inherits positions of key frames of the previous orthodontic treatment plan, and a key frame is a step in which any tooth starts or stops a movement.

In some embodiments, the method for generating restarted orthodontic treatment plan may further comprise: for each tooth to be repositioned, identifying one from the first group of 3D digital models of teeth in which the pose of the tooth to be repositioned is closest to its pose in the first 3D digital model; generating a repositioning path of the tooth to be repositioned, based on its pose in the first 3D tooth digital model and the identified one to the last one of the first group of 3D digital models of teeth; and generating the restarted orthodontic treatment plan based on the repositioning paths of all the teeth to be repositioned.

In some embodiments, the method for generating restarted orthodontic treatment plan may further comprise: selecting, from the dentition, at least one tooth as an anchor tooth which is stationary or to be moved by a small amount in the previous orthodontic treatment plan; and aligning the first 3D digital model of teeth with the 3D digital models of teeth in the initial orthodontic treatment plan with the anchor tooth as reference, wherein the identifying is performed on the basis of the alignments.

In some embodiments, the method for generating restarted orthodontic treatment plan may further comprise: replacing the models of the teeth to be repositioned in the first group of 3D digital models of teeth with corresponding tooth models in the first 3D tooth digital model to obtain the second group of 3D digital models of teeth, the aligning and the identifying are performed based on the second group of 3D digital models of teeth.

In some embodiments, the identifying may be based on numbers of repositioning steps.

BRIEF DESCRIPTION OF THE DRAWINGS

The above and other features of the present application will be illustrated more thoroughly and clearly with reference to the following description and appended claims and figures. It should be appreciated that these figures only show several embodiments of the present disclosure, so they should not be construed as limiting the protection scope of the present application. The content of the present application will be described more clearly and in more details with reference to the figures.

FIG. 1 schematically illustrates a flow chart of a method for generating restarted orthodontic treatment plan according to one embodiment of the present application;

FIG. 1A schematically illustrates a flow chart of 101 shown in FIG. 1 according to one embodiment of the present application;

FIG. 1B schematically illustrates a flow chart of 103 shown in FIG. 1 according to one embodiment of the present application;

FIG. 2 schematically illustrates two 3D digital models of teeth aligned based on an anchor tooth in one example of the present application;

DETAILED DESCRIPTION OF ILLUSTRATED EMBODIMENTS

Figure 3:
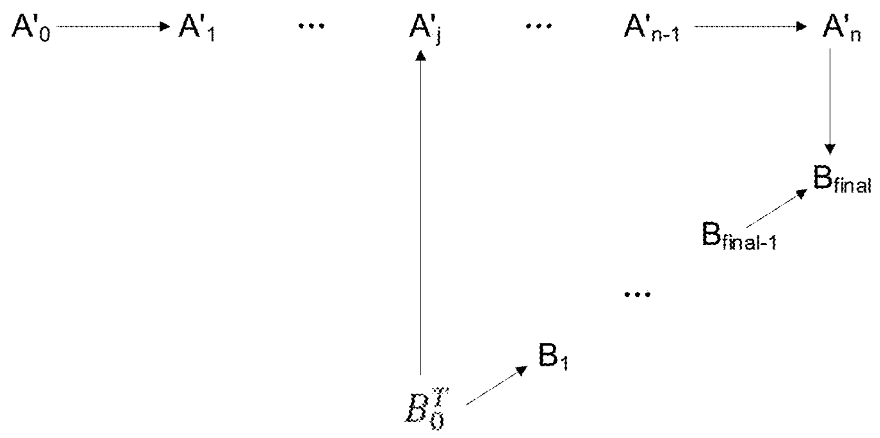
FIG. 3 schematically illustrates the relationship between a restarted orthodontic treatment plan and an initial orthodontic treatment plan according to one embodiment of the present application.

In the following detailed depictions, reference is made to the accompanying drawings, which form a part thereof. In the figures, like reference numbers usually represent like components unless otherwise specified in the context. Exemplary embodiments in the detailed descriptions, figures and claims are not meant to be limiting the protection scope of the present application. Other embodiments may be utilized and other changes may be made to the depicted embodiments, without departing from the spirit or scope of the present application. It will be readily understood that aspects of the present application described and illustrated herein can be arranged, replaced, combined, separated and designed in a wide variety of different configurations, all of which are explicitly contemplated and make part of the present application.

An orthodontic treatment using shell-shaped tooth repositioners requires a series of successive shell-shaped tooth repositioners. These shell-shaped tooth repositioners are worn sequentially to incrementally reposition the patient's dentition from an initial tooth arrangement to a first intermediate tooth arrangement, a second intermediate tooth arrangement . . . a final intermediate tooth arrangement and a target tooth arrangement.

Each shell-shaped tooth repositioner corresponds to one repositioning step and is used to reposition the patient's teeth from an initial tooth arrangement of the repositioning step to a target tooth arrangement of the repositioning step. Usually, a shell-shaped tooth repositioner is a one-piece shell and forms a cavity for receiving teeth. The geometry of the cavity substantially matches the target tooth arrangement of the corresponding repositioning step. Shell-shaped tooth repositioners are fabricated based on target tooth arrangements of corresponding repositioning steps.

Designing shell-shaped tooth repositioners is synonymous with designing an orthodontic plan/path. An orthodontic treatment plan using shell-shaped tooth repositioners is usually referred to as a teeth alignment plan which includes a plurality of successive tooth arrangements from the first intermediate tooth arrangement, the second intermediate tooth arrangement . . . the final intermediate tooth arrangement until the target tooth arrangement.

As mentioned above, in an orthodontic treatment using shell-shaped tooth repositioners, a patient's tooth arrangement might significantly deviate from an initial orthodontic treatment plan so that the patient cannot continue to use the design of shell-shaped tooth repositioners of subsequent phases of the orthodontic treatment plan. At this time, it is necessary to redesign subsequent shell-shaped tooth repositioners, namely, a subsequent teeth alignment plan, based on the patient's current situation. The initially-made teeth alignment plan may be referred to as the initial teeth alignment plan, and the new teeth alignment plan may be referred to as the restarted teeth alignment plan. A teeth alignment plan includes a plurality of successive tooth arrangements.

To overcome the drawbacks of conventional methods for generating restarted teeth alignment plan, the inventors of the present application developed a method for generating restarted teeth alignment plan using a computing device. The method aims to generate a restarted teeth alignment plan based on an initial teeth alignment plan.

For illustrative purpose, the method for generating restarted teeth alignment plan will be described below by taking a dentition of a single jaw (an upper jaw or a lower jaw) as an example.

Figures 1, 1A:
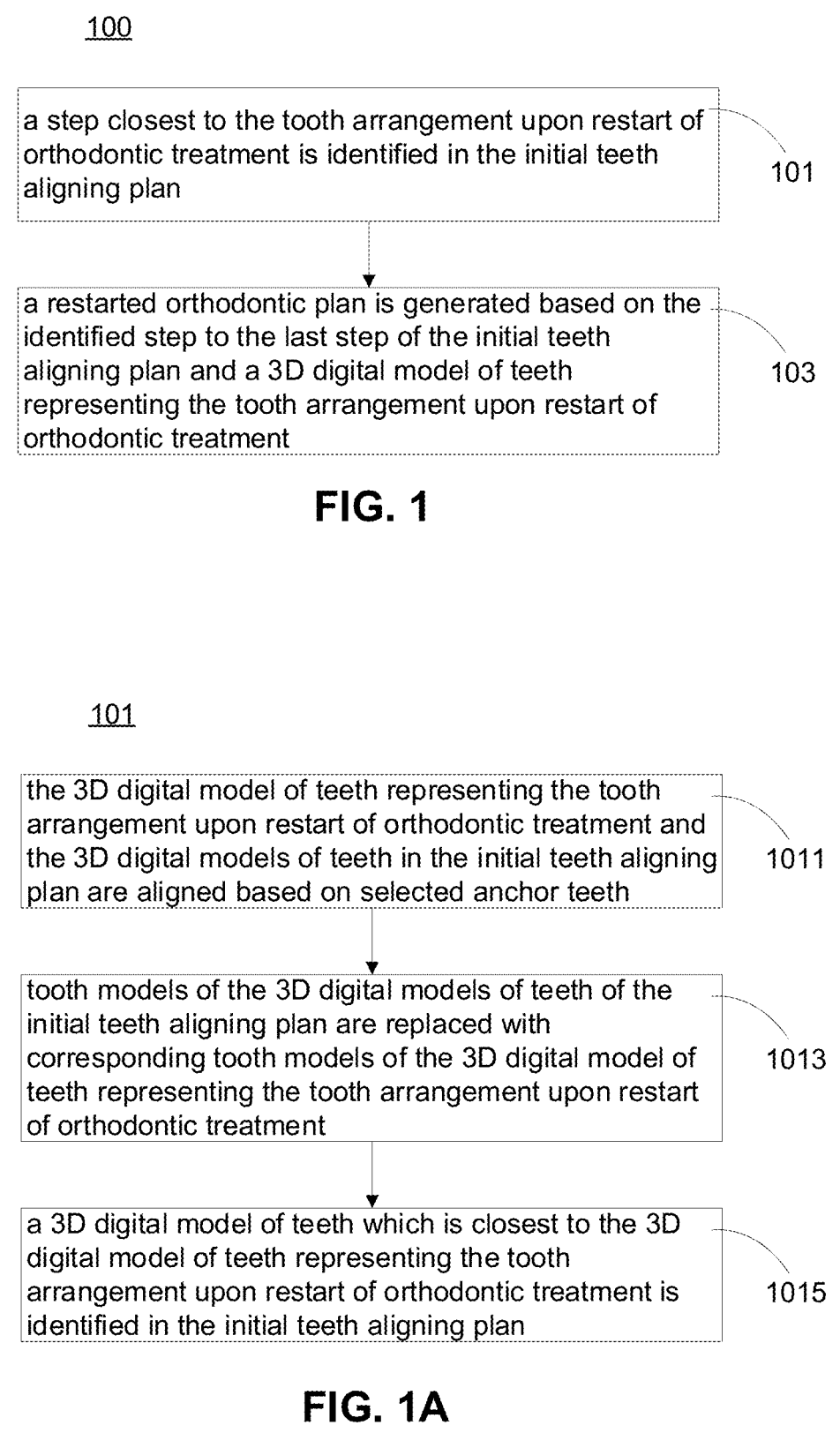

Referring to FIG. 1, it is a schematic flow chart of a method 100 for generating restarted orthodontic treatment plan according to one embodiment of the present application.

Before generating a restarted orthodontic treatment plan, it is needed to identify in the initial orthodontic treatment plan a tooth arrangement (repositioning step) closest to the patient's current tooth arrangement, to minimize the number of steps of the restarted orthodontic treatment plan.

In 101, a repositioning step closest to the tooth arrangement upon restart of the orthodontic treatment is identified from the initial orthodontic treatment plan.

A tooth arrangement is an ordered arrangement of teeth in 3D space, and it includes the geometry and position information of each tooth. Given $\{A_0, A_1, A_2, \ldots, A_{n-1}, A_n\}$ stands for the patient's initial orthodontic treatment plan, and $B_0$ stands for the patient's current tooth arrangement upon restart of orthodontic treatment.

In one embodiment, an Iterative Closest Point (ICP) algorithm may be used to perform point cloud registration between a 3D digital model representing $B_0$ and each of 3D digital models representing $A_0$~$A_n$ respectively, and a Root Mean Square Error (RSME) of two sets of point cloud is calculated after each registration, as an index indicating a similarity of the two sets of point cloud. Therefore, a tooth arrangement having a minimum RSME after registration with the patient's current tooth arrangement may be selected as the tooth arrangement closest to the patient's current tooth arrangement.

The inventors of the present application discovered that as for point cloud registration, an objective function of the ICP algorithm is to minimize the overall RSME between point cloud models. In factual situations, it is common that parts of teeth remain stationary during the whole orthodontic treatment, and the tooth arrangement with the minimum overall RSME is not necessarily the closest tooth arrangement. Furthermore, when step sizes of movements of teeth are given, a distance between two tooth arrangements may be represented by the number of repositioning steps needed to change from one tooth arrangement to another. Obviously, this is dictated by a tooth with the largest number of repositioning steps between the two tooth arrangements, and the RSME is not the most appropriate index for indicating the distance between the two tooth arrangements.

In view of this, the inventors of the present application developed a new method for determining the closest tooth arrangement.

Referring to FIG. 1A, it is a schematic flow chart of 101 according to one embodiment of the present application.

In 1011, based on selected anchor tooth/teeth, a 3D digital model representing the tooth arrangement upon restart of orthodontic treatment is aligned with a 3D digital model of teeth of the initial orthodontic treatment plan.

A 3D digital model representing a tooth arrangement is obtained by a 3D model scanning technology. The world coordinate systems of two 3D digital models generated by two independent scans might not overlap completely, and an error between the 3D digital models representing the two tooth arrangements such caused is a global error.

Since $\{A_0, A_1, A_2, \ldots, A_{n-1}, A_n\}$ and $B_0$ are from two independent scans, global error exists inevitably. Therefore, the global error between the two may be eliminated by performing a series of rigid space transformations on $B_0$, to make the world coordinate system corresponding to $B_0$ close to that of $\{A_0, A_1, A_2, \ldots, A_{n-1}, A_n\}$ as much as possible.

In one embodiment, ICP algorithm may be used to register a certain tooth arrangement $A_i$ in the initial orthodontic treatment plan with $B_0$, to eliminate the global error between the two. At this time, the two point cloud models used in the registration are no longer comprised of all teeth, and instead, only a portion of teeth that remain stationary or have a small movement in the initial orthodontic treatment plan are selected as anchor teeth to generate the point cloud models corresponding to $A_i$ and $B_0$. A rigid transformation matrix $T_i$ of $B_0$ is obtained through the registration, and $B_0$ after the transformation by $T_i$ is denoted as $$B_0^i.$$

Then, the non-anchor teeth in $$B_0^i$$

and $A_i$ are converted into point cloud models, and a maximum distance $$d_{max}^i$$

between each pair of points of the two models is calculated.

In one embodiment, each tooth arrangement in $\{A_0, A_1, A_2, \ldots, A_{n-1}, A_n\}$ may be registered with $B_0$ based on the anchor teeth, and a corresponding rigid transformation matrix and $d_{max}$ of $B_0$ are calculated, and the rigid transformation matrix corresponding to the minimum $d_{max}$ is denoted as T, and is taken as an "optimal" rigid transformation matrix. The operation is to roughly find the tooth arrangement most similar to $B_0$ from the initial orthodontic treatment plan, and to eliminate the global error based on the tooth arrangement. The inventors of the present application discovered after extensive experiments that the operation indeed can improve the precision of the whole method. The $B_0$ after the transformation by T is denoted as $$B_0^T.$$

At this time, it is approximately believed that the global error between $$B_0^T$$

and $\{A_0, A_1, A_2, \ldots, A_{n-1}, A_n\}$ is eliminated.

Referring to FIG. 2, it is an interface of a computer program developed by the inventors of the present application which shows a positional relationship between $B_0$ after the transformation by T and the corresponding tooth arrangement in the initial orthodontic treatment plan in one embodiment.

In 1013, tooth models of the 3D digital models of teeth in the initial orthodontic treatment plan are replaced with models of corresponding teeth of the 3D digital model of teeth representing the tooth arrangement upon restart orthodontic treatment.

Then, the tooth arrangement closest to $B_0$ needs to be found from the initial orthodontic treatment plan. There might be local differences caused by scans between two scans of teeth ($A_0$ and $B_0$), or shapes of the teeth already changed for example due to factors such as wear and growth etc., between the time points the two scans are performed. Therefore, to more accurately select the tooth arrangement closest to $B_0$ from the initial orthodontic treatment plan, tooth models of the tooth arrangement in the initial orthodontic treatment plan may be replaced with tooth models obtained from the latest scan, that is to say, the 3D digital model of each tooth in the tooth arrangements in the initial orthodontic treatment plan is replaced with a 3D digital model of a corresponding tooth in $B_0$.

In one embodiment, the replacement of the tooth models may be carried out as follows. Individual teeth numbered the same in $$B_0^T$$

and $A_i$ are registered using ICP algorithm, a point cloud model of a tooth in $$B_0^T$$

is set as a source model, and a point cloud model of a tooth having the same number in $A_i$ is set as a target model. After the replacement, an initial orthodontic treatment plan $\{A'_0, A'_1, A'_2, \ldots, A'_{n-1}, A'_n\}$ with replaced tooth models is obtained.

In 1015, a 3D digital model of teeth closest to the 3D digital model of teeth representing the tooth arrangement upon restart of orthodontic treatment is identified from the 3D digital models of teeth of the initial orthodontic treatment plan with the replaced tooth models.

Then, for each tooth arrangement in $\{A'_0, A'_1, A'_2, \ldots, A'_{n-1}, A'_n\}$, a minimum number of steps minStep that it takes to change from $$B_0^T$$

to the tooth arrangement is calculated based on step size(s) of tooth movement(s). It is understood that the minimum number of steps of the transformation from one tooth arrangement to another is determined by the tooth having the maximum number of repositioning steps. Then, a tooth arrangement $A'_j$ having the minimum minStep is selected from $\{A'_0, A'_1, A'_2, \ldots, A'_{n-1}, A'\}$ as the tooth arrangement closest to $$B_0^T,$$

and the tooth arrangement closest to $$B_0^T$$

in the initial orthodontic treatment plan is tooth arrangement $A_j$ accordingly.

It is understood that tooth movement step sizes may comprise a translation step size, a torque step size and a rotation step size. Different step sizes may be set for different teeth. A tooth movement step size represents an amount of movement of a tooth that can be achieved by each step when shell-shaped tooth repositioners are used for orthodontic treatment.

After the tooth arrangement $A_j$ closest to $$B_0^T$$

is selected, the restarted orthodontic treatment plan may be generated based on $\{A_j, A_{j+1}, \ldots, A_{n-1}, A_n\}$.

In one embodiment, a range where the tooth arrangement closest to $$B_0^T$$

lies in may be estimated. The identifying may be performed only for the tooth arrangements within the range, to reduce computational load.

In some cases, restart might be performed multiple times in the whole orthodontic treatment process. The initial orthodontic treatment plan refers to the previous orthodontic treatment plan upon the restart.

In 103, the restarted orthodontic treatment plan is generated based on a section from the selected step to the last step in the initial orthodontic treatment plan and the 3D digital model of teeth representing the tooth arrangement upon the restart of orthodontic treatment.

Referring to FIG. 1B, it is a schematic flow chart of 103 according to one embodiment of the present application.

In 1031, the 3D digital model of teeth representing the target tooth arrangement of the initial orthodontic treatment plan with the replaced tooth models is optimized in terms of collision and gap, to obtain the 3D digital model of teeth representing the target tooth arrangement of the restarted orthodontic treatment plan.

The target tooth arrangement $A_n$ in the initial orthodontic treatment plan may be directly taken as the target tooth arrangement of the restarted orthodontic treatment plan if there is no special circumstance. However, as for the target tooth arrangement $A'_n$ of the initial orthodontic treatment plan with the replaced tooth models, since it is replacement of individual tooth models, there might be unreasonable collision(s) and gap(s) between adjacent teeth after the model replacement. Therefore, $A'_n$ shall not be directly taken as the target tooth arrangement.

In one embodiment, $A'_n$ may be optimized in terms of collision and gap based on current enamel reduction information to bring it in compliance with requirements. In one embodiment, $A'_n$ may be optimized in terms of collision and gap based on the following constraint conditions:

(1) non-collision constraint: the constraint is for a pair of adjacent teeth, whose interproximal surfaces both have already undergone enamel reduction, or each shall not undergo enamel reduction;

(2) constraint on a maximum allowable collision amount: the constraint allows a collision between a pair of adjacent teeth, for which enamel reduction is allowed, but the amount of collision may not exceed a given value $C_{max}$;

(3) zero-gap constraint: if there is no special circumstance such as space needs to be reserved for an implant, a gap between adjacent teeth beyond a reasonable range is not allowed; and (4) constraint of keeping molars stationary: the constraint is for a case in which molars need to remain stationary, during the optimization, the positions of the molars shall not change.

A basic principle of the optimization in terms of collision and gap is that with the dental arch curve remains unchanged, positions of a plurality of teeth to be repositioned are adjusted along the dental arch curve according to the constraints so that collisions and gaps between all adjacent teeth satisfy the constraints.

In one embodiment, when position of a tooth is adjusted along the dental arch curve, an angle between the X-axis of the local coordinate system of the tooth and a tangent vector of the dental arch curve is kept unchanged so that the labial/buccal surface of the tooth remains facing outward.

In one embodiment, the optimization in terms of collision and gap may comprise a series of adjustments of distances between interproximal surfaces of adjacent teeth. Here, adjustment of distance between interproximal surfaces of a pair of adjacent teeth may be considered as a basic optimization unit.

A basic optimization unit may be simply described as follows: two adjacent teeth on a given dental arch curve l(s) are numbered as $t_1$ and $t_2$, respectively, their corresponding dental arch curve position parameters are $u_1$ and $u_2$ (a dental arch curve position parameter represents the position of a tooth on a dental arch curve), and an initial distance between the two teeth is do. Given that at least one of $t_1$ and $t_2$ is a tooth to be repositioned, the tooth to be repositioned is moved along the dental arch curve, i.e., the dental arch curve position parameter of the tooth to be repositioned is adjusted so that the distance between $t_1$ and $t_2$ is equal to a given distance parameter d. The distance parameter is a floating point number with a sign. When the sign is positive, this means that there is a gap between adjacent teeth; when the sign is negative, this means that there is collision between the adjacent teeth. In one embodiment, collision and gap between two teeth may be calculated using a 3D digital model collision detection function.

The process of adjusting the distance between $t_1$ and $t_2$ from $d_0$ to d may be considered as solving a non-linear equation, so it may be achieved by Newton secant method through multiple iterations. In a basic optimization unit, if two teeth are both teeth to be repositioned, two adjacent teeth may be moved in a mirrored style in a single-step optimization process, i.e., the two adjacent teeth may be moved simultaneously away from or toward each other by a curve parameter $$\frac{1}{2}|\Delta s|.$$

If only one tooth in the two adjacent teeth is a tooth to be repositioned, then only the tooth to be repositioned is moved by $\Delta s$ along the dental arch curve in the single-step optimization process.

In one embodiment, the optimization in terms of collision and gap may be divided into two phases as the situation demands. The first phase is a general-purpose optimization phase, in which collisions and gaps between stationary molars and their adjacent teeth to be repositioned are not considered. In this phase, adjustment of distances between adjacent teeth may start from two incisors on a single jaw (if an incisor is missing, two teeth with the smallest tooth numbers on both sides may be selected) towards both sides until there is a stationary molar or the last molar.

The distance parameter d may be assigned a value depending on different cases.

Case 1: for two adjacent teeth, if there is enamel reduction not yet performed upon restart of orthodontic treatment, the effective constraint may be the constraint on a maximum allowable collision amount. If $d_0 \geq C_{max}$, let $d=C_{max}$, otherwise let $d=d_0$, and the distance between the two adjacent teeth will not be adjusted.

Case 2: if a large gap is reserved between two adjacent teeth in the target tooth arrangement of the initial orthodontic treatment plan, let $d=d_0$, and the distance between two adjacent teeth will not be adjusted.

Case 3: in other cases, no collision or gap is allowed between adjacent teeth, let d=0.

The optimization process will be described in detail using a single jaw dentition $\{t_{a7}, t_{ab}, \ldots, t_{a1}, t_{b1}, \ldots, t_{b6}, t_{b7}\}$ as an example, wherein $t_{a6}$, $t_{a7}$, $t_{b6}$ and $t_{b7}$ are stationary molars in the initial orthodontic treatment plan.

First, two teeth $t_{a1}$ and $t_{b1}$ (usually, incisors) with the smallest tooth numbers in left and right quadrants are selected, and both are set as teeth to be repositioned, and basic optimization unit is performed on the two teeth according to a corresponding constraint.

Starting from the tooth tai with the smallest tooth number on the left side, a tooth that has already been adjusted is set as stationary state, its adjacent unadjusted tooth $t_{a2}$ on the left side is set as repositionable state, and basic optimization unit may be performed on these two teeth according to a corresponding constraint. After this basic optimization unit, the optimization advances to the next pair of adjacent teeth $\{t_{a2}, t_{a3}\}$ on the left side, and so on, until the adjustment of the last pair of adjacent teeth is completed or next tooth is a stationary molar, namely, $\{t_{a5}, t_{a6}\}$ in the initial orthodontic treatment plan (i.e., the last pair of adjacent teeth on which basic optimization unit is performed is $\{t_{a4}, t_{a5}\}$, and basic optimization unit will not be performed on $\{t_{a5}, t_{a6}\}$). A similar process is performed on the teeth on the right side.

If there is no stationary molar, various constraints on collision and gap have already been satisfied after completion of the general-purpose optimization in the first phase, the optimization in the second phase needn't be performed. Since the optimization in the first phase stops at a stationary tooth, e.g., stops at $\{t_{a5}, t_{a6}\}$ in the above example, the distance between $t_{a5}$ and $t_{a6}$ is uncontrollable, and excessive collision or gap might also occur between them. Therefore, the optimization in the second phase needs to be performed for all the teeth on the jaw to optimize relationships between stationary posterior teeth and their adjacent non-stationary teeth.

In one embodiment, the optimization in the second phase may generally follow the following principle: unexecuted enamel reduction amounts of enamel reduction designs of teeth on the jaw are adjusted so that the neighboring relationship of the stationary posterior teeth satisfies the requirements. If excessive gap or collision is still not eliminated after the designed enamel reduction amounts are adjusted to maximum values, a new enamel reduction design needs to be added to another tooth or a gap between other teeth needs to be increased, so that the relationships between the stationary posterior teeth and their adjacent teeth satisfy the constraints. For a single jaw, there might be stationary molars only on a single side or on both sides.

In one embodiment, during the optimization in terms of collision and gap, the dental midline may remain stationary. The optimization order from the incisors to posterior teeth in the first phase ensures that the dental midline remains stationary. Therefore, a corresponding design is also needed in the second phase to ensure that the dental midline remains stationary during the optimization.

The teeth on a single jaw may be divided by the dental midline into two tooth sequences in two quadrants, namely, $\{t_{a7}, t_{a6}, \ldots, t_{a1}\}$ and $\{t_{b1}, \ldots, t_{b6}, t_{b7}\}$. To ensure that the dental midline does not deviate from the original design, both teeth on two sides of the centerline may be set as stationary teeth. As such, the optimization in the second phase may be abstractly defined as optimizing in terms of collision and gap a group of successive teeth with stationary teeth at both ends according to the constraints. Take the tooth group $\{t_{a6}, t_{a5}, \ldots, t_{a1}\}$ on one side of the dental midline as an example, $t_{a6}$ and tai are both stationary teeth. If excessive gap or collision exist between interproximal surfaces of $\{t_{a5}, t_{a6}\}$, optimization needs to be performed on this pair of teeth.

At this time, unexecuted amounts of the designed enamel reduction of all interproximal surfaces of the tooth group may be adjusted. If there is a gap between $\{t_{a5}, t_{a6}\}$, the pre-designed enamel reduction amount may be reduced, otherwise the pre-designed enamel reduction amount may be increased. If there are a plurality of enamel reduction designs, the enamel reduction amounts of interproximal surfaces may be adjusted in order of their distance from the stationary teeth, a closer one may be adjusted earlier.

It is assumed that there are unexecuted amounts in enamel reduction designs between the interproximal surfaces of $\{t_{a3}, t_{a4}\}$ and $\{t_{a2}, t_{a3}\}$ in the group of teeth $\{t_{a6}, t_{a5}, \ldots, t_{a1}\}$, and the enamel reduction amounts are $ipr_{a34}$ and $ipr_{a23}$, respectively. Given that a desired total enamel reduction adjustment amount is $\Delta ipr$, and the distance between the interproximal surfaces of the stationary molar and its adjacent tooth to be repositioned is $\Delta d_f$. When $\Delta ipr$ is adjusted to an extreme value $\Delta ipr_e$, for example, all enamel reduction designs are cancelled or adjusted to a maximum value (e.g., 0.5 mm), if $\Delta d_f+\Delta ipr_e$ and $\Delta d_f$ are of different signs, this indicates that $\Delta d_f$ may be probably eliminated by adjusting $ipr_{a34}$ and $ipr_{a23}$. The adjustment amount of the enamel reduction design may be determined by solving the following Equation (1):

$$\Delta d_f(\Delta ipr) = 0 \quad \text{Equation (1)}$$

Wherein, Equation (1) is a non-linear equation. Considering the monotonic consistency of the equation nearby the zero point, Newton secant method may be used to solve the equation. When solving the above equation using iterative method, an intermediate iteration step may calculate a corresponding distance $$\Delta d'_f$$

between the interproximal surfaces based on an estimated $\Delta ipr'$, and this can be carried out as follows.

The first step: an enamel reduction adjustment amount $\Delta ipr'$ is assigned. An adjustment amount is first assigned to the interproximal surfaces of $\{t_{a3}, t_{a4}\}$ according to its distance based priority. If there is still allowed adjustment amount after $ipr_{a34}$ is adjusted to a maximum or a minimum value, then it continues to adjust the enamel reduction amount of the interproximal surfaces of $\{t_{a2}, t_{a3}\}$, and so on. Assuming only $\{t_{a3}, t_{a4}\}$ is assigned an enamel reduction amount, then $\Delta ipr_{a34}=\Delta ipr'$.

The second step: all teeth to be repositioned are repositioned according to the adjusted enamel reduction amounts. The order of the repositioning is from incisor to posterior teeth. Except the interproximal surfaces whose enamel reduction amounts are adjusted, the distances between the interproximal surfaces which are previously adjusted in the first time are set invariable.

The third step: a collision engine is used to calculate an excess value $$\Delta d'_f$$

of the interproximal surfaces of $\{t_{a5}, t_{a6}\}$.

When convergence is achieved after multiple iterations, the excess $\Delta d_f$ may be eliminated. However, if $\Delta d_f+\Delta ipr_e$ and $\Delta d_f$ are of the same sign after $\Delta ipr$ is adjusted to an extreme value, this indicates that the $\Delta d_f$ cannot be eliminated only by adjusting existing designed enamel reduction amounts. Then, it is necessary to add new enamel reduction designs or modify gaps for other teeth to be repositioned. Two adjustment methods are provided for two cases respectively, in one of which $\Delta d_f$ is an excess collision value, in another of which $\Delta d_f$ is an excess gap value.

If there is still excess collision when $\Delta d_f<0$, it is necessary to add new enamel reduction designs to interproximal surfaces of teeth, to which no enamel reduction design has been added, to eliminate the excess collision. In one example, a maximum enamel reduction amount of 0.5 mm may be added to a single interproximal surface. Therefore, the excess collision can be completely eliminated in most cases by adding new enamel reduction designs.

First, for interproximal surfaces of $\{t_{a5}, t_{a6}\}$, $t_{a5}$ is in a repositionable state, and $t_{a6}$ is a stationary tooth in the initial orthodontic treatment plan. The input distance parameter d is set as d=0, and the basic optimization unit is performed to eliminate the collision of the interproximal surfaces. Through the operation in this step, the excess collision of $\{t_{a5}, t_{a6}\}$ is transferred to the interproximal surfaces of $\{t_{a4}, t_{a5}\}$. For the interproximal surfaces, first it needs to check whether enamel reduction design may be added thereto. If there are existing enamel reduction designs, or they are not qualified to add enamel reduction, the distance parameter of the interproximal surfaces is set to be consistent with the distance after the adjustment in the first step, the basic optimization unit is performed, and continue to check and adjust next interproximal surfaces. If it is allowed to add new enamel reduction designs, the current distance of the interproximal surfaces is denoted as $d_{a45}$, and the enamel reduction amount $ipr_{a45}$ of the interproximal surfaces is set as $ipr_{a45}=\max(0.5\text{ mm}, d_{a45})$. If $d_{a45}>0.5$ mm, this indicates that it is not enough by only adding the enamel reduction design to the current interproximal surfaces, and it is necessary to set the current input distance parameter of the interproximal surfaces to be 0.5 mm, perform the basic optimization unit, and continue to check next interproximal surfaces. Otherwise, after the addition of the enamel reduction design, the excess collision between the stationary tooth and its adjacent tooth to be repositioned is completely eliminated. If there are no interproximal surfaces to which new enamel reduction design can be added, or the collision of the interproximal surfaces still cannot be eliminated after the new enamel reduction designs are added, the excess collision amount may be evenly allocated to each interproximal surface, i.e., a distance change amount Δd of each interproximal surface is calculated to make the following Equation (2) satisfied:

$$\Delta d_f(\Delta d) - \Delta d = 0 \quad \text{Equation (2)}$$

The equation may be solved using Newton secant method after convergence is achieved by iteration. After the excess collision amount is allocated to each interproximal surface, since the collision of a single interproximal surface is very small, this may be considered an over correction and still satisfies medical requirements.

If $\Delta d_f>0$, there is an excess gap. First, if there is a large gap reserved for an implant or for subsequent correction, then the gap between the interproximal surfaces of the stationary tooth and its adjacent tooth may be "transferred" to the reserved large gap. The operation of "transferring" the gap is similar to the previous operation of "transferring" the collision. Starting from the elimination of the gap between the interproximal surfaces of $\{t_{a5}, t_{a6}\}$, the basic optimization unit with distances between interproximal surfaces unchanged is performed on the interproximal surfaces from side a to side b, and the process stops until there is the reserved large gap between the current interproximal surfaces.

If there is no reserved large gap, the excess gap can only be evenly allocated to the interproximal surfaces of all teeth to be repositioned. In one embodiment, this operation may be implemented as follows: given the distance increment of interproximal surface of each tooth to be repositioned is Δd, make the above Equation (2) satisfied, and Δd can be calculated by solving the equation.

Similar to calculation of the total enamel reduction adjustment amount in the previous step, Δd may also be calculated using Newton secant method after convergence is achieved by iteration. After the excess $d_f$ is evenly allocated to each interproximal surface, since its amount is very small, it may be believed that the adjusted tooth arrangement meets medical requirements.

After the above optimization in terms of collision and gap, the tooth arrangement $A'_n$ with replaced tooth models becomes a target tooth arrangement that meets medical requirements, and the new target tooth arrangement is marked as $B_{final}$.

In 1033, the restarted orthodontic treatment plan is generated based on the 3D digital models of teeth representing the initial tooth arrangement and target tooth arrangement of the restarted orthodontic treatment plan and a section selected from the initial orthodontic treatment plan.

Referring to FIG. 3, it schematically illustrates the relationship between a restarted orthodontic treatment plan and an initial orthodontic treatment plan according to one embodiment of the present application.

As known from FIG. 3, in one embodiment, the restarted orthodontic treatment plan from $$B_0^T$$

to $B_{final}$ may be divided into three parts: part one is from $$B_0^T$$

to $A'_j$, part two is from $A'_j$ to $A'_n$, and part three is from $A'_n$ to $B_{final}$.

To reduce the number of steps of the restarted orthodontic treatment plan, in one embodiment, the above "polyline" style path may not be used, instead, a difference between $$B_0^T$$

and $A'_j$ and a difference between $A'_n$ and $B_{final}$ may be allocated to corresponding steps, to omit part one and part three in the above "polyline" style path, and generate a "slant line" style path from $$B_0^T$$

to $B_{final}$, namely, $$\{B_0^T, B_1, \ldots, B_{final-1}, B_{final}\}.$$

In the initial orthodontic treatment plan, each tooth has certain ranges of steps, only in which it moves, to satisfy some medical constraints. Therefore, reference may be made to the initial orthodontic treatment plan to prevent a tooth from moving back and forth after it reaches a target pose. For example, if repositioning of a tooth ends at a step (i.e., the tooth reaches its target position at this step, and remains stationary in subsequent steps) in the initial orthodontic treatment plan, the corresponding step is taken as an ending step of the repositioning of the tooth in the restarted orthodontic treatment plan.

In addition, in the initial orthodontic treatment plan, some steps are set as key steps (or referred to as key frames). In one orthodontic treatment plan, if a step is a starting step or stopping step of a movement mode of any tooth, the step is a key step. In one embodiment, the restarted orthodontic treatment plan inherits positions of key frames of the previous orthodontic treatment plan.

On the one hand, some key steps are considered as being prone to excess collision, so collision check and optimization need to be performed for these key steps, to make the steps of the whole initial orthodontic treatment plan meet requirements on collision. On the other hand, some key steps are steps, at which repositioning of some teeth start or stop (e.g., the repositioning of a tooth is started or stopped at a certain key step), and this contains starting and stopping information of the teeth. Therefore, in generation of the "slant line" style path from $$B_0^T$$

to $B_{final}$, it allows the corresponding steps in the slant line style path to inherit the information of the key steps in the initial orthodontic treatment plan, to ensure that the slant line style path satisfies medical constraints that the initial orthodontic treatment plan satisfies.

In one embodiment, a container C may be created to store steps of the generated slant line style path. Let an initial step Co in the container C be $$B_0^T,$$

and search for key steps from $A'_{j+1}$. When a key step $A'_k$ is found, the position of each tooth in a step of the slant line style path corresponding to $A'_k$ may be calculated.

For a tooth $t_i$, if the step $A'_k$ is not within one of ranges, at the start and end of each of these ranges a movement of the tooth starts and stops, i.e., the tooth $t_i$ remains stationary in the step $A'_k$, the position of the tooth may be set consistent with its position in the last step stored in the container C.

If the step $A'_k$ is within a range, at the start and end of the range a movement of the tooth $t_i$ starts and stops, a relative transformation matrix of the positions of the tooth $t_i$ between $A'_k$ and a corresponding step of the slant line style path may be calculated based on the differences of the positions of the tooth $t_i$ between $$B_0^T$$

and $A'_j$ and between $A'_n$ and $B_{final}$, and the position of the tooth $t_i$ in the corresponding step of the slant line style path may be obtained by transformation.

The position of the tooth $t_i$ in the step $$A'_k$$

is denoted as $$loc_i^k,$$

and the position of the tooth $t_i$ in step $$A'_j$$

is denoted as $$loc_i^j.$$

Let $T_h$ be the relative transformation matrix from $$loc_i^j \text{ to } loc_i^k.$$

The position of the tooth $t_i$ in the initial step $$B_0^T$$

of the restarted orthodontic treatment plan is denoted as $$loc_i^{original},$$

and a linear interpolation between $$loc_i^k \text{ and } loc_i^{original}$$

is denoted as $$V_i^0(u),$$

and an interpolation coefficient is as expressed in the following Equation (3):

$$V_0(u) = (1-u)loc_i^{original} + u \cdot loc_i^j \qquad \text{Equation (3)}$$

wherein $$u = \frac{n_{cur}}{n_{total}} \qquad \text{Equation (4)}$$

wherein $n_{cur}$ is the number of repositioning steps that the tooth has already completed till the step $$A'_k,$$

and $n_{total}$ is a total number of repositioning steps (stationary steps are excluded) of the tooth from $$A'_j \text{ to } A'_k.$$

Then, a relative transformation matrix $T_{v0}$ of the position of the tooth $t_i$ between $$B_0^T$$

and $A'_j$ may be calculated, and a relative transformation matrix $T_{v1}$ of the position of the tooth $t_i$ between $A'_n$ and $B_{final}$ may be calculated.

Then, the position of the tooth $t_i$ in the step of the slant line style path corresponding to the step $$A'_k$$

may be calculated according to the following Equation (5):

$$loc_i = T_{v1} T_h T_{v0} loc_i^{original} \quad \text{Equation (5)}$$

By the above method, the position of each tooth in the current key step may be calculated to obtain a complete key step denoted as Ck.

In one embodiment, the generated key step may be optimized in terms of collision to ensure it satisfies relevant constraints. A method similar to the above optimization method may be used. In one embodiment, since the objects to be optimized are different, the above optimization method may be modified in the following aspects in terms of settings and constraints:

1. In a generated key step, not all teeth are within a repositioning range, and part of teeth remains stationary. Therefore, this part of teeth not within their repositioning ranges is kept stationary during the optimization.
2. For the generated key step, the existence of excess gap is acceptable, so the optimization process is only for excess collision.
3. In the generated key step, if an interproximal surface has an enamel reduction design not yet executed, the collision amount shall not exceed the corresponding designed enamel reduction amount.

In a step of the restarted orthodontic treatment plan, there might be a plurality of groups of adjacent moving teeth separated by stationary teeth. For the moving tooth groups, to satisfy constraints, only the second phase optimization in the collision optimization method needs to be performed, and the optimization of the gap may be skipped. Then, the optimized key step is pushed back to the container C.

The above operation is repeated until the last key step in $\{A'_j, A'_{j+1}, \ldots, A'_{n-1}, A'_n\}$. Since the last key step is the target tooth arrangement, it just needs to store the target tooth arrangement $B_{final}$ of the restarted orthodontic treatment plan in the container C. As such, all key steps (including the initial tooth arrangement $$B_0^T$$

and the target tooth arrangement $B_{final}$) of the restarted orthodontic treatment plan are obtained.

Then, all steps of the restarted orthodontic treatment plan from the initial tooth arrangement $$B_0^T$$

to the target tooth arrangement $B_{final}$ may be obtained by adding steps between all key steps of the restarted orthodontic treatment plan by linear interpolation based on step sizes of movements of the teeth.

It is understood that due to the difference between $$B_0^T$$

and $A'_j$ and the difference between $A'_n$ and $B_{final}$, the number of steps of the restarted orthodontic treatment plan may be different from $\{A'_j, A'_{j+1}, \ldots, A'_{n-1}, A'_n\}$.

Inspired by the present application, it is understood that $A_j$ may not be the step closest to $B_0$, it may be a step before or after the step closest to $B_0$, or may be selected based on $B_0$ according to other medical requirements.

In the above embodiments, the search for the step closest to the tooth arrangement upon restart in the previous orthodontic treatment plan and the generation of the restarted orthodontic treatment plan are both preformed based on the whole dentition. In a further embodiment, the search for the most similar step and the generation of the restarted orthodontic treatment plan may also be performed based on a single tooth. The embodiment will be described in detail below.

Figure 4:
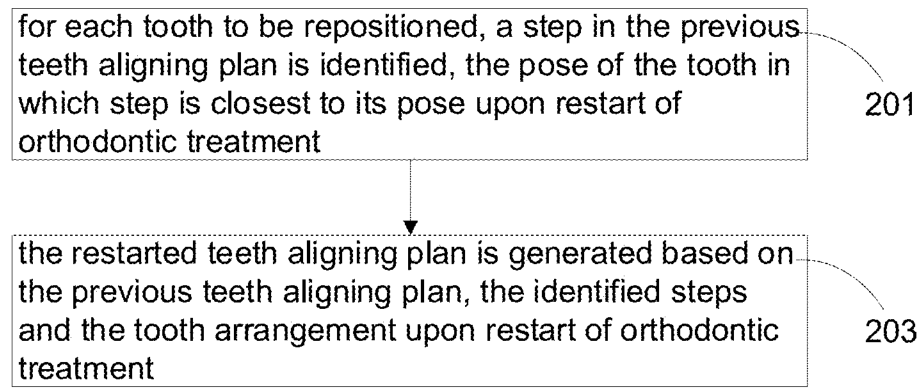
FIG. 4 schematically illustrates a flow chart of a method for generating restarted orthodontic treatment plan according to another embodiment of the present application.

Referring to FIG. 4, it is a schematic flow chart of a method 200 for generating a restarted orthodontic treatment plan according to another embodiment of the present application.

In 201, for each tooth to be repositioned, a step in the previous orthodontic treatment plan, in which step its pose is closest to its pose upon the restart of the orthodontic treatment, is identified.

Similar to the embodiment based on the whole dentition, alignment may be performed based on the anchor teeth before the identifying to eliminate global error between the 3D digital model representing the tooth arrangements upon the restart of the orthodontic treatment and the 3D digital models representing the tooth arrangements in the previous orthodontic treatment plan. Then, the tooth models in the 3D digital models representing the tooth arrangements in the previous orthodontic treatment plan are replaced with corresponding tooth models in the 3D digital models representing the tooth arrangement upon the restart of the orthodontic treatment, to obtain a series of 3D digital models with replaced tooth models. Then, for each tooth to be repositioned, a step in the initial orthodontic treatment plan, in which step the pose of the tooth is closest to its pose upon the restart of the orthodontic treatment, is identified.

In one embodiment, to avoid back and forth movement of a tooth in the restarted orthodontic treatment, a step in which the pose of the tooth is closest to the target pose and is closer than its pose upon restart of the orthodontic treatment, may be selected, that is to say, if the pose of the tooth to be repositioned upon restart of the orthodontic treatment is between two steps of the previous orthodontic treatment plan, the later step may be selected as the closest step.

In one embodiment, a tooth to be repositioned might remain stationary in a range in the previous orthodontic treatment plan, that is to say, the pose of the tooth is the same in all steps in the range of the previous orthodontic treatment plan. If the pose of the tooth at $$B_0^T$$

is closest to the first step in the range, the last step in the range may be taken as the step in which the pose of the tooth is closest to its pose at $$B_0^T$$

In 203, a restarted orthodontic treatment plan is generated based on the previous orthodontic treatment plan, the selected closest steps and the tooth arrangement upon restart of the orthodontic treatment.

First, the 3D digital model of teeth representing the target tooth arrangement of the previous orthodontic treatment plan after the replacement of the tooth models may be optimized in terms of the collision and gap, to obtain the 3D digital model teeth representing the target tooth arrangement of the restarted orthodontic treatment plan. The same optimization method as the above may be used.

For tooth $t_s$, given that the step in which the pose of the tooth in the previous orthodontic treatment plan is closest to its pose upon restart of the orthodontic treatment plan is $$A'_{js}.$$

Similar to the above, the repositioning path of the tooth $t_s$ from its pose in $$B_0^T$$

to its pose in $B_{final}$ may be divided into three parts: the first part is from its pose in $$B_0^T$$

to its pose in $A'_{js}$, the second part is from its pose in $A'_{js}$ to its pose in $A'_n$, and the third part is from its pose in $A'_n$ to its pose in $B_{final}$.

Similarly, to reduce the number of steps of the restarted orthodontic treatment plan, the repositioning path of the tooth $t_s$ in the restarted orthodontic treatment shall not use the abovementioned "polyline" style path, instead, the pose difference of the tooth $t_s$ between $$B_0^T$$

and $A'_{js}$ and the pose difference of the tooth $t_s$ between $A'_n$ and $B_{final}$ are allocated to corresponding steps, to generate a "slant line" style repositioning path of the tooth $t_s$ from $$B_0^T$$

to $B_{final}$.

Similar to the above embodiment of generating the restarted orthodontic treatment plan based on the whole dentition, in the embodiment of generating the restarted orthodontic treatment plan based on individual teeth, reference may also be made to the key frames of the tooth $t_s$ in the previous orthodontic treatment plan in the generation of the repositioning path of the tooth $t_s$, i.e., the starting and stopping steps of the repositioning of the tooth $t_s$ in the restarted orthodontic treatment plan correspond to those in the previous orthodontic treatment plan.

In one embodiment, the repositioning path of the tooth $t_s$, i.e., the pose of the tooth $t_s$ in each step of the restarted orthodontic treatment plan, may be calculated using the same method as the above embodiment of generating the restarted orthodontic treatment plan based on the whole dentition.

After the restarted repositioning paths of all teeth to be repositioned are obtained, the restarted orthodontic treatment plan may be generated based on these restarted repositioning paths.

After the restarted orthodontic treatment plan is obtained, the 3D digital models representing a series of successive tooth arrangements may be used to control an apparatus to fabricate corresponding shell-shaped tooth repositioners for subsequent orthodontic treatment.

It is understood that in many cases, step, tooth arrangement and 3D digital model of teeth may refer to one another.

Inspired by the present application, it is understood that unless otherwise specified, the above operations can all be performed by a computer device (e.g., a computer and any suitable other computing devices), so that a lot of manpower cost can be saved, and the efficiency can be improved.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

Likewise, the various diagrams may depict an example architecture or other configuration for the disclosed method and system, which is done to aid in understanding the features and functionality that can be included in the disclosed method and system. The claimed invention is not restricted to the illustrated example architectures or configurations, but the desired features can be implemented using a variety of alternative architectures and configurations. Additionally, with regard to flow diagrams, operational descriptions and method claims, the order in which the blocks are presented herein shall not mandate that various embodiments be implemented to perform the recited functionality in the same order unless the context dictates otherwise.

Unless the context dictates, terms used herein are generally intended as "open" terms instead of limiting. The use of phrases such as "one or more", "at least" and "but not limited to" should not be construed to imply that the parts of the present application that do not use similar phrases intend to be limiting.

What is claimed is:

1. A computer-implemented method for generating restarted orthodontic treatment plan, comprising:

obtaining a first group of M 3D digital models of teeth which respectively represent the last M successive tooth arrangements in a previous orthodontic treatment plan of a dentition;

obtaining a first 3D digital model of teeth which represents the tooth arrangement of the dentition upon restart of orthodontic treatment;

replacing at least one tooth model in the first group of 3D digital models of teeth with corresponding tooth model in the first 3D digital model of teeth, to obtain a second group of M 3D digital models of teeth;

performing collision and gap optimization on the last one 3D digital model of teeth in the second group of 3D digital models of teeth to obtain a second 3D digital model of teeth representing a target tooth arrangement of a restarted orthodontic treatment plan;

identifying a 3D digital model of teeth in the second group of 3D digital models of teeth, of which the tooth arrangement is closest to the first 3D digital model;

calculating key frames of the restarted orthodontic treatment plan based on pose differences of teeth to be repositioned between the first 3D digital model of teeth and the identified 3D digital model of teeth, pose differences between the identified 3D digital model of teeth and corresponding key frames of the second group of 3D digital model of teeth, and pose differences of the teeth to be repositioned between the second 3D digital model of teeth and the last one of the second group of 3D digital models of teeth;

interpolating based on the poses of the teeth to be repositioned of the corresponding key frames of the restarted orthodontic treatment plan, to obtain other steps of the restarted orthodontic treatment plan, wherein a key frame is a step in which any tooth starts or stops a movement, M is a natural number greater than 2, and an orthodontic treatment plan comprises a plurality of successive tooth arrangements from an initial tooth arrangement to a target tooth arrangement, and represents the path of orthodontic treatment; and fabricating a plurality of successive shell-shaped tooth repositioners based on corresponding successive steps of the restarted orthodontic treatment plan.

2. The method of claim 1, wherein the replacement of the at least one tooth model is based on an ICP algorithm.

3. The method of claim 1, wherein the number of steps of the restarted orthodontic treatment plan is same as the number of 3D digital models of teeth from the identified one to the last one of the second group of 3D digital models of teeth.

4. The method of claim 1, wherein each key frame of the restarted orthodontic treatment plan is calculated based on additional variables including: a sequence number of the current key frame along the restarted orthodontic treatment plan, and a total number of steps of the restarted orthodontic treatment plan.

* * * * *